(12) United States Patent
Hagrud

(10) Patent No.: US 6,463,850 B1
(45) Date of Patent: Oct. 15, 2002

(54) METHOD AND MEANS FOR FORMING LOCALLY COMPRESSED REGIONS ON ABSORBENT PRODUCTS

(75) Inventor: Ulrika Hagrud, Gothenburg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/446,260

(22) PCT Filed: Jun. 8, 1998

(86) PCT No.: PCT/SE98/01096

§ 371 (c)(1),
(2), (4) Date: Mar. 13, 2000

(87) PCT Pub. No.: WO98/58612

PCT Pub. Date: Dec. 30, 1998

(30) Foreign Application Priority Data

Jun. 25, 1997 (SE) .............................................. 9702430

(51) Int. Cl.$^7$ .............................................. B30B 15/34
(52) U.S. Cl. .............................. 100/38; 100/73; 100/74; 100/92; 100/327; 156/209
(58) Field of Search .............................. 100/38, 73, 74, 100/92, 315, 317, 318, 320, 327, 328; 156/209, 238, 239, 240; 604/380, 365, 366, 367, 378, 379, 370

(56) References Cited

U.S. PATENT DOCUMENTS

| | | | | |
|---|---|---|---|---|
| 1,429,865 A | * | 9/1922 | Friedman | 100/73 |
| 3,373,679 A | * | 3/1968 | French | 100/74 |
| 3,570,491 A | * | 3/1971 | Sneider | 604/366 |
| 3,607,391 A | * | 9/1971 | Shann | 100/74 |
| 3,721,242 A | | 3/1973 | Krusko | |
| 3,838,694 A | * | 10/1974 | Mesek | 604/370 |
| 4,518,451 A | * | 5/1985 | Luceri et al. | 156/209 |
| 4,612,081 A | * | 9/1986 | Kasper et al. | 100/315 |
| 5,195,428 A | * | 3/1993 | Gawlitta et al. | 100/73 |
| 5,483,873 A | * | 1/1996 | Koivukunnas et al. | 100/74 |
| 5,674,341 A | * | 10/1997 | Ng | 156/240 |
| 5,799,572 A | * | 9/1998 | Campbell et al. | 100/74 |

FOREIGN PATENT DOCUMENTS

| | | |
|---|---|---|
| EP | 0 229 542 | 7/1987 |
| EP | 0 373 974 | 6/1990 |
| WO | WO 94/26091 | * 11/1994 |
| WO | WO 95/11649 | 5/1995 |

* cited by examiner

Primary Examiner—Stephen F. Gerrity
Assistant Examiner—Louis Huynh
(74) Attorney, Agent, or Firm—Young & Thompson

(57) ABSTRACT

Method and device for forming local compressions (7) in a material (31) wherein moisture (17) is applied locally to the areas being compressed during the compression operation.

16 Claims, 2 Drawing Sheets

METHOD AND MEANS FOR FORMING LOCALLY COMPRESSED REGIONS ON ABSORBENT PRODUCTS

CROSS REFERENCE TO RELATED APPLICATION

This is the 35 USC 371 national stage of international application PCT/SE98/01096, filed on Jun. 8, 1998 which designated the United States of America.

FIELD OF THE INVENTION

The present invention relates to a method and a device for forming locally compressed regions on absorbent products.

BACKGROUND OF THE INVENTION

Absorbent products, in particular female hygiene products, e.g. panty liners, sanitary napkins, etc. and diapers and incontinence protection products, are usually provided with fold lines which help control the shape that the product takes up during use. These fold lines can be produced by selectively compressing some or all of the material comprised in the absorbent product in order to form lines of locally compressed material. These lines of compressed material can, for example in a panty liner, be placed in the longitudinal direction and given an anatomically adapted shape. During use the panty liner is easily deformed into a bowl-like shape which more closely conforms to the anatomy of the user and thereby is more comfortable to wear and provides greater security against leakage. Local compressions can also act as trenches which prevent or reduces the spread of fluid laterally, thereby reducing leakage. In certain materials the compressed material in the compression lines has an increased capillary action which helps distribute the fluid better in the longitudinal direction.

Compression lines can be formed on the finished product or can be formed only on a constituent part, e.g. an absorbent body, before it is incorporated into a product.

It is often difficult to produce permanent compression lines in absorbent products, especially if they comprise absorbent bodies made of resilient material such as e.g. chemithermomechanical pulp (CTMP), chemical pulp, polymers or the like. These resilient fibres tend to return to their uncompressed shape after having been compressed and the compression lines become impermanent. One way of making the effects of the compression more permanent is to increase the moisture content of the item being compressed. This can be achieved by increasing the environmental humidity in the machine where the compressing takes place and/or by directly spraying water or some other fluid onto the material before it is fed into the forming machine. The increased humidity can lead to chemical bonds forming between fibres which are in contact with each other.

EP-A 0 678 608 describes a method for manufacturing an absorbent fibre layer for use in such products, in which a surface of said layer is provided with a pattern of compressed regions. The compressed regions are formed by moistening the lower surface of the fibre layer and compressing it by hot-calendering. The moistening is performed by a water nozzle or a steam box which supplies moisture to substantially the whole of the web.

Raising the moisture content of the material in this way can lead to negative consequences: the material can become sticky and fasten in moulds and onto transfer rollers leading to increased down-time while the machinery is cleaned. This increased stickiness can lead to the material clumping together which means that the risk that hard spots can occur in the product also increases. In addition some of the added moisture can be absorbed by superabsorbent particles or liquids (i.e. products able to absorb many times their own weight of liquid) in the material which naturally reduces their ability to absorb body fluids later.

SUMMARY OF THE INVENTION

An object of the present invention is to provide a method which can produce permanent compression lines in a material without the disadvantages of previous know methods.

A further object of the present invention is provide absorbent products with permanent compression lines.

The objects of the present invention are achieved by locally moistening the material in which compression lines are to be formed only in the regions intended to form compression lines. In a method according to the invention this is achieved by providing the compression means which forms the compression lines with openings through which moisture can be provided only to the material intended to be compressed during the compression operation.

BRIEF DESCRIPTION OF THE DRAWINGS

In the following, the invention will be described by means of examples of embodiments with referenced to the accompanying drawings, in which.

DETAILED DESCRIPTION OF THE INVENTION

Figure 1:
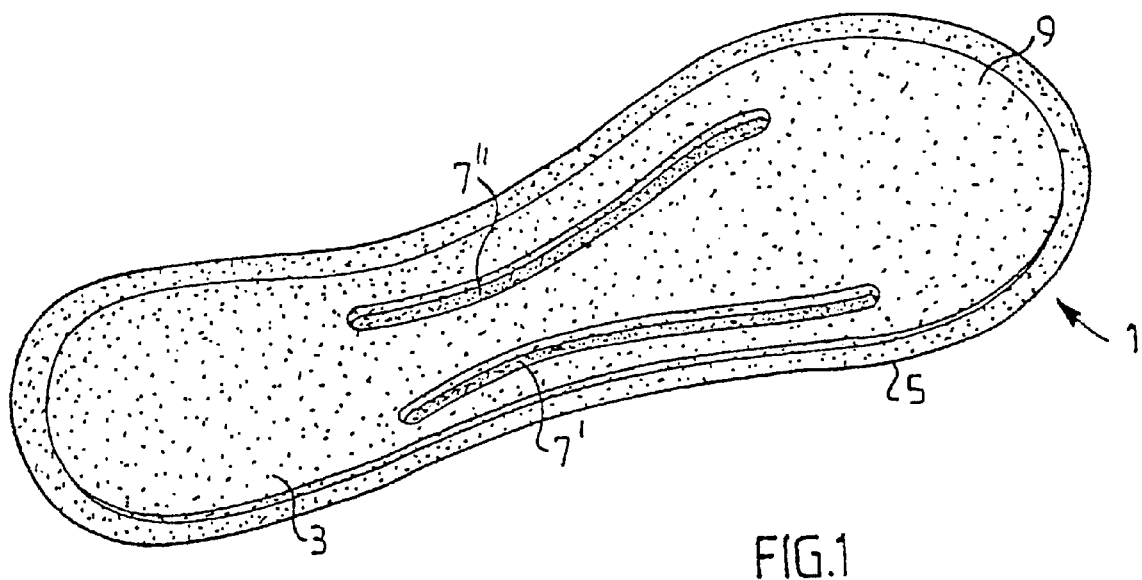
FIG. 1 shows a perspective view of a panty liner with fold-lines.

FIG. 1 shows a panty-liner 1 which comprises an absorbent body 3 mounted on a liquid-impermeable bottom layer 5. There are fold lines 7', 7", formed of locally compressed absorbent body material 9, present in the absorbent body 3. The absorbent body material 9 can be any suitable absorbent material such as natural or artificial fibres with or without superabsorbents. The absorbent body is normally cut out of a web of absorbent material.

Figure 2:
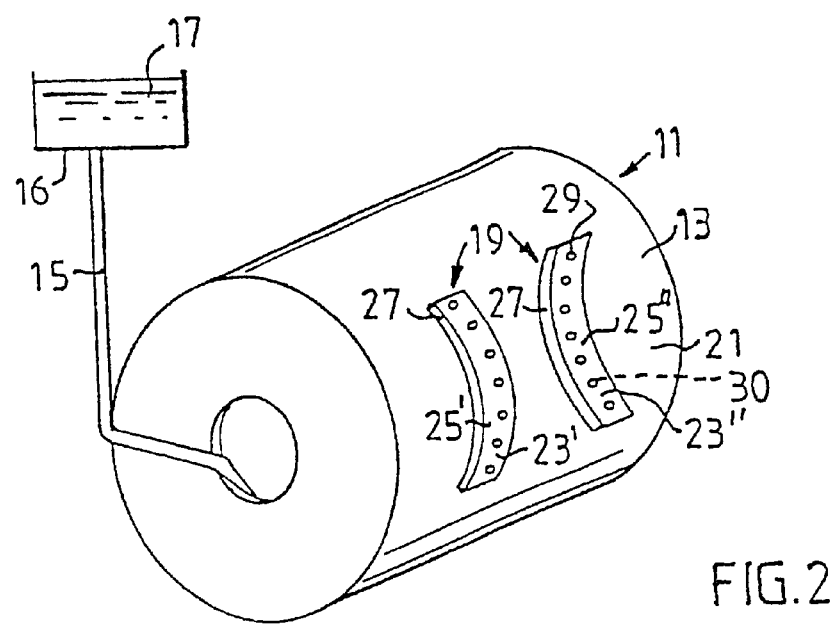
FIG. 2 shows a perspective view of a roller according to the invention.

FIG. 2 shows schematically a roller 11 for forming locally compressed fold lines 7', 7". Roller 11 has a substantially cylindrical body 13 which during use rotates around its longitudinal axis. In this embodiment roller 11 is hollow and is provided with means 15 for supplying it with a moistening fluid 17 from a fluid reservoir 16. Roller 11 is equipped with projecting press means 19 which extend out from the cylindrical surface 21 of the roller 11. In this embodiment press means 19 is shown as a pair of curved projecting bodies 23', 23" with faces 25', 25" which lie in a curved plane substantially parallel with the plane of the surface 21 of the roller, and curved sides 27. Faces 25', 25" are provided with moisture emitting holes 29. Holes 29 are provided with valve means 30 which control the flow of moisture through holes 29. Preferably the amount of fluid supplied is regulated to give a moisture content of between 10% and 30%, most preferably between 15% and 20%.

Figure 3:
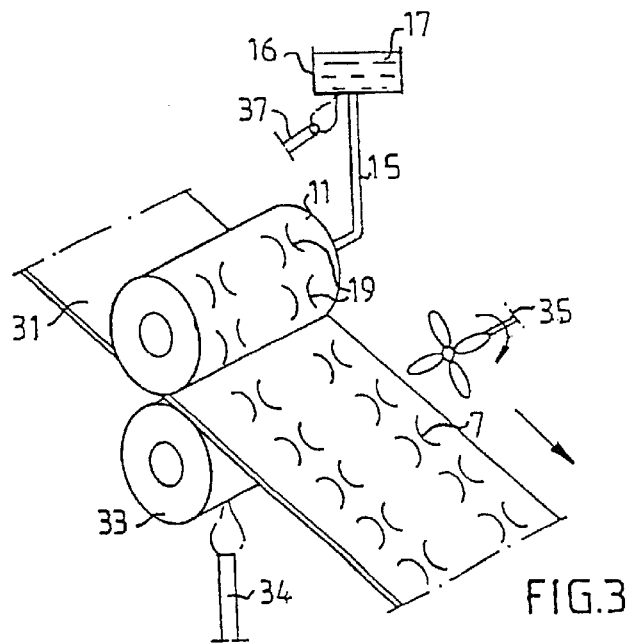
FIG. 3 shows a perspective view of a web of material being treated with a roller according to the invention.

FIG. 3 shows schematically in perspective a first embodiment of an arrangement for performing the method in accordance with the invention. A web 31 of absorbent material is rolled between a roller 11 and a counter-roller 33 with a plain surface. In this embodiment roller 11 is provided with two lines of projecting press means 19 which project out from its surface. Roller 11 and counter-roller 33 are mounted substantially parallel to each other and separated by distance which is less than or equal to the thickness of the web 31. The web 31 passes between roller 11 and counter-roller 33 and the faces 25', 25" of the press means 19 compress the material of the web between the faces and the counter-roller to form local compressions 7 which can subsequently be used as fold lines 7 when absorbent bodies are cut out of the web material. At the same time as the web material is compressed, fluid is emitted through fluid emitting holes 29 in sufficient amounts to moisturise the web material being compressed in the local compressions 7. The holes 29 can be provided with valve means 30 which allow moisture to be emitted during the compression operation, which, for example in the embodiment shown in FIG. 3, means that fluid is only allowed to be emitted when the faces 25', 25" are facing vertically downwards. This material locally compressed between the faces 25', 25" of the press means 19 and counter-roller 33 then forms the fold lines. Roller 11 preferably rotates with a peripheral speed which is the same as the linear speed of web 31 which thereby prevents the press means 19 tearing or stretching the web 31. In a preferred embodiment of the invention roller 11 and counter roller 33 are heated by any suitable roller heating means 34, shown schematically as a flame 34, so that the material of the web 31 is more easily compressed and the rollers 11, 33 could be followed by cooling means, shown schematically as a fan 35, which cools down the material of the web 31 before it can spring back into its original shape. It is also conceivable that the fluid 17 is heated by any suitable heating means 37, shown schematically as a flame 37, as well as, or instead of, the roller and/or counter-roller.

It is conceivable that the counter-roller can be replaced by a stationary counter-surface (not shown).

Figure 4:
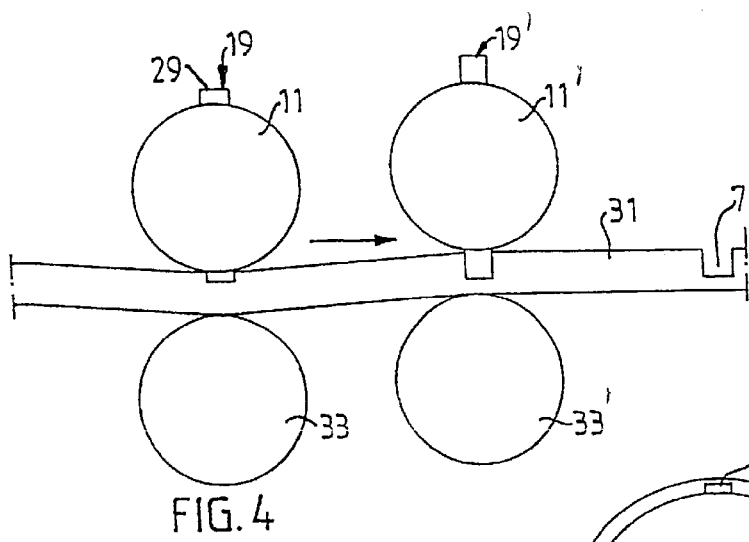
FIG. 4 shows schematically a side view of a second embodiment of a roller arrangement for performing the method in accordance with the invention.

FIG. 4 shows schematically a side view of a second embodiment of a roller arrangement for performing the method in accordance with the invention. In this embodiment a web 31 of absorbent material passes between two sets of rollers 11, 11' and counter-rollers 33, 33'. The first roller 11 is provided with two lines of projecting press means 19 which project out from its surface a distance d while the second roller 11' is provides with two lines of projecting press means 19'" which project out from its surface a distance d' which is greater than distance d. The cylindrical surfaces of rollers 11 and 11' have the same diameter and rollers 11 and 11' are spaced a distance apart which corresponds to an integral number times the distance between the projecting press means 19, 19'. The rotation of the rollers 11, 11' is synchronised so that the depressions made in the surface of the web by projecting press means 19 on roller 11 are made deeper by the projecting press means 19' on roller 11'. In other words the projecting press means 19' are superimposed on the local compressions made by projecting press means 19. As in the previous embodiment, as the web material is compressed by roller 11, fluid is emitted through fluid emitting holes 29 in sufficient amounts to moisturise the web material being compressed in the local compressions 7. The locally compressed web material is able to absorb the fluid during the time it is being transported between rollers 11 and 11' before it is further compressed by projecting press means 19' on roller 11'. This leads to better defined local compressions.

In a further embodiment of the invention (not shown) roller 11' is also provided with fluid emitting means by means of which extra fluid can be provided to the local compressions if necessary.

While the rollers have been described as having cylindrical surfaces with identical diameters it is of course possible to have different sized rollers and to adapt the number and position of their projecting means to achieve the required superimposed local compressions produced by the rollers e.g. one roller could be twice the size of the other roller and be provided with twice as many projecting means. It is also conceivable to use more than two rollers and to use them to provide a plurality of different fluids to local compressions.

Figure 5:
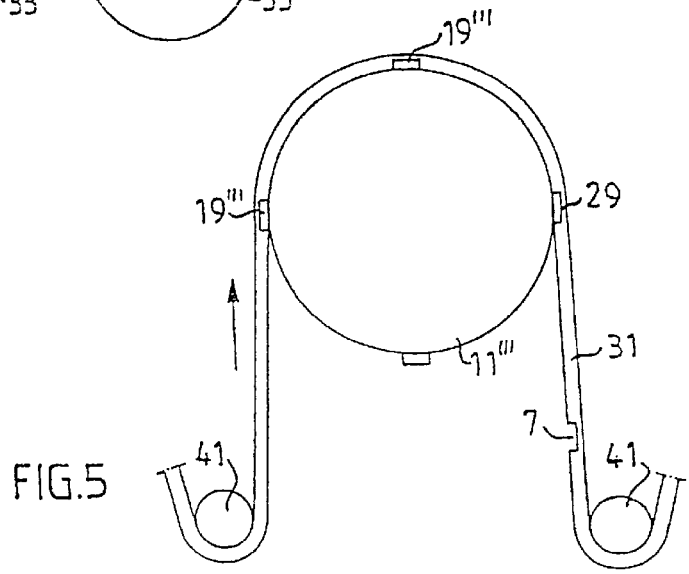
FIG. 5 shows schematically a side view of a third embodiment of a roller arrangement for performing the method in accordance with the invention.

FIG. 5 shows schematically a side view of a third embodiment of a roller arrangement for performing the method in accordance with the invention. In this embodiment a web of material is fed over a rotating compression roller 11'" which projects out of the plane of the web material. The circumferential velocity of the roller 11'" is substantially the same as the web materials rate of movement so that the web material in contact with the roller 11'" does not slip on the roller. Guide rollers 41 on either side of the roller 11'" guide the web material so that it substantially covers half of the cylindrical surface of the roller 11'". Thus each part of the web material 31 is in contact with the roller 11'" for the time it takes the roller to complete one half of a revolution. The roller is provided with projecting means 19'". The web material is under tension and the portions of the web material which are in contact with the projecting means 19'" are compressed against the projecting means by the tension in the web and form local compressions 7. As in the previous embodiment, as the web material is compressed by roller 11'", fluid is emitted through fluid emitting holes 29 in the projecting means 19'" in sufficient amounts to moisturise the web material being compressed in the local compressions 7. The locally compressed web material is able to absorb the fluid during the time it takes rollers 11'" to rotate through one half of a revolution. This leads to better defined local compressions.

In a further embodiment of the invention the counter-surface or counter-roller is provided with cavities (not shown) corresponding to the press means of the roller in order to allow embossing of the web material.

In another embodiment of the invention the counter-surface or the counter-roller is provided with projections corresponding to the press means of the roller in order to allow double-sided compressing of the web material. In a preferred variation of this embodiment both the roller and the counter-surface or counter-roller are provided with moisture emitting means.

Although the press means have been illustrated by example which are intended to leave local compressions/fold lines of uniform depth and a curved shape it is naturally possible to adapt the shape of the press means such that local compressions of any desired shape and/or depth profile can be achieved in any type of product and compressible material. For example the faces of the press means could vary in height with respect to the surface of the roller such that the local compressions become shallower towards their ends, or vice versa. Local compressions can also be formed as straight lines. Although the embodiments shown in the figures show the local compressions arranged as mirror-image pairs they can be arranged in any possible orientation and number. Thus, for example, a panty liner could comprise two or more pairs of mirror-image local compressions arranged in parallel. Local compressions can be arranged symmetrically, asymmetrically, as mirror-image pairs or singularly as required.

The holes for emitting fluid can be any suitable shape and number and the valve means can be any sort of valve e.g. rotary, ball, reed, etc. which can be operated, automatically or manually, by any suitable means e.g. gravity operated, cam-actuated, electrically controlled, magnetically controlled. The valve means are preferably metered so that the quantity of fluid emitted is only just sufficient to moisten the material which is intended to be compressed. The moisture can be supplied as a fluid (e.g. plain water or water with an additive such as Kymene 617™ or vapour (e.g. steam) and the valves can be situated in any suitable position e.g. adjacent to the emitting holes or between the holes and a fluid reservoir.

The invention has been illustrated by examples in which the moisture emitting holes are provided on the face of the press means, but it is also conceivable that the press means could be provided with moisture emitting holes on the sides of the press means. The moisture does not have to be emitted by holes in the roller(s) but can be provided using any suitable technique, for example, techniques known from the printing and/or glue application industries.

Although the invention has been illustrated by examples showing how local compression can be formed in webs of material passing under a roller before the material has been cut out, the invention is also applicable to manufacturing methods in which individual cut-out or otherwise formed products are stamped, rolled or otherwise local compressed with the local addition of moisture in the areas being locally compressed.

What is claimed is:

1. Method for forming a pattern of compression in a material for absorbent products, which comprises the steps of:
   providing at least one compression structure having an outer compression surface and including press means projecting from said outer compression surface; said press means having moisture emitting holes;
   locally compressing the material with said press means to form at least one local pattern of compression; and
   locally supplying moisture to the material via said moisture emitting holes only in a patterned region corresponding to the pattern of compression during said compressing step.

2. The method according to claim 1, wherein additional moisture is supplied to said material via a counter-roller or counter-surface.

3. The method according to claim 2, wherein said counter-roller or counter-surface is heated.

4. The method according to claim 1, wherein said press means is heated.

5. The method according to claim 1, further comprising the step of cooling said pattern of compression.

6. Apparatus for forming a pattern of compression in a material for absorbent products, which comprises:
   at least one compression structure having an outer compression surface and including press means projecting from said outer compression surface of said compression structure;
   said press means structured and arranged to form at least one local pattern of compression;
   said press means having moisture emitting holes therein which are operatively connectable to a source of moistening fluid, said moisture emitting holes, in use, emitting moisture only to a patterned region corresponding to the pattern of compression.

7. The apparatus according to claim 6, further comprising a counter-surface or counter-roller; said counter-surface or counter-roller comprising moisture emitting means.

8. The apparatus according to claim 6, further comprising valve means for controlling the supply of a fluid to said moisture emitting holes.

9. The apparatus according to claim 6, wherein said at least one compression structure is a roller or stamping plate.

10. The apparatus according to claim 6, further comprising heater means for heating said press means.

11. The apparatus according to claim 6, further comprising heater means for heating moisture emitted by said moisture emitting holes.

12. The apparatus according to claim 6, further comprising cooling means for cooling said local pattern of compression.

13. Apparatus for forming a pattern of compression in a material for absorbent products, which comprises:
   at least one compression structure having an outer compression surface and including press means projecting from said outer compression surface of said compression structure;
   said press means structured and arranged to form at least one local pattern of compression;
   said press means having moisture emitting holes therein which are operatively connectable to a source of moistening fluid, said moisture emitting holes, in use, emitting moisture only to a patterned region corresponding to the pattern of compression, and at least one of counter-surface and counter-roller means, which comprise moisture emitting means.

14. The apparatus according to claim 13, further comprising heater means for heating said press means.

15. The apparatus according to claim 13, further comprising heater means for heating moisture emitted by said moisture emitting holes.

16. The apparatus according to claim 13, further comprising cooling means for cooling said local pattern of compression.

* * * * *